(12) United States Patent
Nam

(10) Patent No.: US 8,637,098 B2
(45) Date of Patent: Jan. 28, 2014

(54) NATURAL PLANT EXTRACT COMPOSITION FOR PREVENTION AND RECOVERY OF HYPERLIPIDEMIA AND STROKE, NATURAL TEA CONTAINING THE SAME AS ACTIVE INGREDIENT AND METHOD FOR PREPARING THE NATURAL TEA

(75) Inventor: Jong Hyun Nam, Seoul (KR)

(73) Assignee: Jong Hyun Nam, Seoul (KR)

( * ) Notice: Subject to any disclaimer, the term of this patent is extended or adjusted under 35 U.S.C. 154(b) by 796 days.

(21) Appl. No.: 12/235,764

(22) Filed: Sep. 23, 2008

(65) Prior Publication Data

US 2009/0098223 A1  Apr. 16, 2009

(51) Int. Cl.
- *A61K 36/482* (2006.01)
- *A61K 36/484* (2006.01)
- *A61K 36/605* (2006.01)
- *A61K 36/79* (2006.01)

(52) U.S. Cl.
USPC ........................................................ 424/777

(58) Field of Classification Search
None
See application file for complete search history.

(56) References Cited

U.S. PATENT DOCUMENTS

| | | | |
|---|---|---|---|
| 5,674,498 A | 10/1997 | Inoue et al. | |
| 6,933,291 B2 * | 8/2005 | Qi et al. | 514/171 |
| 2004/0044067 A1 | 3/2004 | Pan | |

FOREIGN PATENT DOCUMENTS

| | | |
|---|---|---|
| CN | 1631382 A | 6/2005 |
| JP | 08012585 A | 1/1996 |
| JP | 2000128798 A | 5/2000 |
| JP | 2002291460 A | 10/2002 |
| JP | 2003073279 A * | 3/2003 |
| JP | 2003206225 A | 7/2003 |
| JP | 2005343808 A | 12/2005 |
| KR | 1020010109708 A | 12/2001 |
| KR | 1020020061587 A | 7/2002 |
| KR | 1020040031495 A | 4/2004 |
| KR | 1020060007105 A | 1/2006 |
| WO | WO-0160390 A1 | 8/2001 |
| WO | WO-02060390 A2 | 8/2002 |

OTHER PUBLICATIONS http://davesgarden.com/guides/pf/go/1764/.*
Mulberry 2005, http://www.immortalitea.com/mulberry.htm.*
Enkhmaa et al., Mulberry (*Morus alba* L.) Leaves and Their major Flavonol Quercetin 3-(6-Malonylglucoside) Attentuate Atherosclerotic Lesion Development in LDL Receptor-Deficient Mice, 2005, J Nutr, 135: 729-734.*
Masella et al., Extra Virgin Olive Oil Biophenols Inhibit Cell-mediated Oxidation of LDL by Increasing the mRNA Transcription of Glutathione-Related Enzymes, 2004, J Nutr, 134: 785-791.*

* cited by examiner

*Primary Examiner* — Patricia Leith
*Assistant Examiner* — Catheryne Chen
(74) *Attorney, Agent, or Firm* — IpHorgen Ltd.

(57) ABSTRACT

A natural plant extract composition for the recovery and prevention of hyperlipidemia and stroke, a natural tea comprising the same as an active ingredient, and a method for preparing the natural tea. The natural plant extract composition contains a *Cassia tora* extract and an *Albizzia julibrissin* extract. The natural plant extract composition can lower the blood cholesterol level to prevent arteriosclerosis and also can prevent stroke, which is caused by the increase in the blood cholesterol content. Also, it can help recovery from the disease through the continued drinking thereof even after the onset of the disease, and when prepared into a drink, it is easy to drink so that it can be taken at ordinary times, and thus is effective for the prevention and treatment of hyperlipidemia and stroke.

12 Claims, No Drawings

US 8,637,098 B2

NATURAL PLANT EXTRACT COMPOSITION FOR PREVENTION AND RECOVERY OF HYPERLIPIDEMIA AND STROKE, NATURAL TEA CONTAINING THE SAME AS ACTIVE INGREDIENT AND METHOD FOR PREPARING THE NATURAL TEA

BACKGROUND OF THE INVENTION

1. Technical Field

The present invention relates to a natural plant extract composition for the recovery and prevention of hyperlipidemia and stroke, a natural tea containing the same as an active ingredient, and a method for preparing the natural tea, and more particularly to a natural extract, i.e., a natural plant extract comprising a *Cassia tora* extract and an *Albizzia julibrissin* extract.

2. Background Art

Diseases of the circulatory system are now the main causes of death not only in USA and Europe but also in Korea, and particularly mortality rates by ischemic heart diseases (angina and myocardial infarction), as arteriosclerotic diseases, and cerebrovascular diseases, are greatly increasing. An increase in blood cholesterol and lipid levels tends to cause arteriosclerosis, which is a cardiovascular disease that interferes with blood flow by hypercholesterolemia to be able to cause heart attack, stroke and the like. An excessive intake of cholesterol caused by excessive nutrient intake resulting from an improvement in the eating environment of a modern person remains after satisfying cell requirements in the body. Such cholesterol is transported by low-density lipoprotein (LDL) while it is deposited on the inner membrane of blood vessels and also converted into foam cells, fatty streaks, atheroms and the like, which lower vasoconstriction and vasodilation abilities to cause coronary artery disease, stroke, peripheral vascular stenosis, hypertension and the like. The foam cells are repeatedly subjected to inflammatory reaction and cell growth while they break or thicken the vascular wall, so that blood platelets adhere to the wall to cause thrombosis. As a result of this process, the supply of blood to the heart is instantaneously blocked due to the stenosis of blood vessels by arteriosclerosis and the total occlusion of blood vessels by thrombosis, thus inducing death by myocardial infarction.

Accordingly, the prevention of cardiovascular diseases is of more importance than the treatment thereof, and thus there have been many studies on the treatment of hyperlipidemia and therefore arteriosclerosis and stroke. Among these studies, studies on soluble dietary fibers that can lower cholesterol levels have been conducted, but studies on natural extracts having low side effects have not shown satisfactory results.

Accordingly, the present inventors have conducted studies to develop food which can lower cholesterol levels through the constant administration thereof (because the prevention of hyperlipidemia and stroke are of more importance than the treatment thereof, as described above), and thus can prevent hyperlipidemia and therefore arteriosclerosis, stroke, etc., and also help the treatment of the diseases even after the onset thereof and, as a result, found a natural extract which is easy to drink while having excellent effects, thereby completing the present invention.

SUMMARY OF THE INVENTION

Accordingly, it is an object of the present invention to provide a natural plant extract composition effective for the recovery and prevention of hyperlipidemia and stroke, and a natural tea containing the same as an active ingredient.

Another object of the present invention is to provide methods for preparing a natural plant extract composition effective for the recovery and prevention of hyperlipidemia and stroke, and a natural tea containing the same as an active ingredient.

To achieve the above objects, the present invention provides a natural plant extract composition for the recovery and prevention of hyperlipidemia and stroke, which comprises a *Cassia tora* extract and an *Albizzia julibrissin* extract.

In the inventive composition, the *Cassia tora* extract and the *Albizzia julibrissin* extract are contained in a weight ratio of 1:0.3-5.

The *Albizzia julibrissin* extract can contain a large amount of quercitrin.

The *Cassia tora* extract can contain a large amount of obtusin ($C_{18}H_{16}O_7$).

The natural plant extract composition may additionally comprise at least one selected from the group consisting of *Schizandra chinensis* extract, *Morus alba* extract and licorice extract. Said at least one plant extract selected from the group consisting of *Schizandra chinensis* extract, *Morus alba* extract and licorice extract can be contained in a weight ratio of 1:0.1-2 with respect to the *Albizzia julibrissin* extract.

In addition to the above plant extracts, the natural plant extract composition may additionally comprise other natural plant extracts.

The natural plant extract composition can comprise 20-50 wt % of the *Cassia tora* extract, 10-70 wt % of the *Albizzia julibrissin* extract, and 10-20 wt % of at least one natural plant extract selected from the group consisting of *Schizandra chinensis* extract, *Morus alba* extract and licorice extract. Also, the natural plant extract composition may comprise 20-50 wt % of the *Cassia tora* extract, 10-65 wt % of the *Albizzia julibrissin* extract, 5-20 wt % of the *Schizandra chinensis* extract, 5-20 wt % of the *Morus alba* extract and 5-20 wt % of the licorice extract.

As an extraction solvent in the present invention, any conventional extraction solvent can be used, and it is particularly preferable to use a mixed solvent of 50% alcohol and water (1:1-3). The natural plant extracts is prepared by extraction at 80-100° C. for about 1-8 hours, but is not limited thereto. Each of the extracts can be prepared by extracting each of the plants 1-3 times, mixing the extract fractions with each other and concentrating the mixture before use.

The *Albizzia julibrissin* extract can be obtained from the bark, leaf, flower, root and seed of *Albizzia julibrissin*.

The *Albizzia julibrissin* extract is obtained by washing *Albizzia julibrissin*, completely drying the washed plant, physically crushing the dried plant and extracting the crushed material with an extraction solvent. As the extraction solvent, any conventional extraction solvent can be used, and it is preferable to use a mixed solvent of 50% alcohol and water. The extract can be obtained by performing extraction at 80-100° C. for 1-8 hours and then evaporating ethanol. The solvent for the extraction of *Albizzia julibrissin* is used in a weight ratio of 1:2-6 with respect to the crushed *Albizzia julibrissin*.

The *Cassia tora* extract is obtained in the same manner as the *Albizzia julibrissin* extract; however, a solvent for the extraction of *Cassia tora* is preferably used in a weight ratio of 1:2-6 with respect to the crushed *Cassia tora*. The *Cassia tora* extract can be obtained from the leaf, root, stem and flower of *Cassia tora*.

The *Schizandra chinensis* extract, the *Morus alba* extract and the licorice extract can be obtained in the same manner as the *Albizzia julibrissin* extract.

The natural plant extract composition can be contained in various foods to prepare natural teas effective for the recovery and prevention of hyperlipidemia and stroke, and is particularly contained in drinking water for easy drinking.

The natural tea may contain general food additives, including a softener, a fragrance, a preservative and an antioxidant.

The natural tea effective against hyperlipidemia and stroke preferably contains the inventive natural plant extract composition in an amount of 14-40 wt % based on the total weight thereof.

The natural tea preferably contains antioxidant vitamins, particularly vitamin E.

In another aspect, the present invention provides methods for preparing a natural plant extract composition for the recovery and prevention of hyperlipidemia and stroke and for preparing a natural tea containing the same as an active ingredient, the method comprising the steps of: preparing a *Cassia tora* extract; preparing an *Albizzia julibrissin* extract; and concentrating and mixing said extracts, wherein the extracts are prepared by extraction with a mixed solvent of 50% alcohol and water at 80-100° C. for 1-8 hours.

The inventive method may further comprise the step of preparing a *Schizandra chinensis* extract, preparing a *Morus alba* extract or preparing a licorice extract.

DETAILED DESCRIPTION OF THE PREFERRED EMBODIMENTS

Hereinafter, the present invention will be described in further detail.

The present invention relates to a natural plant extract composition effective for the recovery and prevention of hyperlipedemia and stroke, comprising SR *Albizzia julibrissin* extract and a *Cassia tora* extract, as well as a natural tea containing the same as an active ingredient. In the inventive composition, the *Albizzia julibrissin* extract and the *Cassia tora* extract are preferably contained in a weight ratio of 1:0.3-5.

*Albizzia julibrissin* Dura is also called "Boochenamu", "Sanyazanamu", "Sos-salbabnamu", "Jagunamu", "Jagulnang" (Jeju, Korea), "Zagusari", "Shoisalbab" (Youngnam, Korea), "Yahapsoo", and "Haphonsoo", in the Korean language. It has twice-pinnately compound leaves. The leaves stick together at night and open at the daylight. Tufts of pink flowers appear along the tops of the branches. Its fruits are bean shell-like in shape. It grows at mountains and fields, 500-700 m above the sea level, in the central and southern parts of Korea, and is planted in parks or around houses in various parts. Because its leaves stick together at night, it also called "Yahap" or "Haphon" in the Korean language. It contains alkaloids, tannins and saponins in the bark, quercitrin in the leaf, 200 mg % vitamin C in the young leaf, and alkaloids in the seed. Also, it contains glycoside albitosin. The specific component "quercitrin" acts to enlarge capillary vessels, and to make the skin clean and to neutralize a poison from the skin. In addition, as recorded in the Tang Materia Medica (Tang Ben Cao) authored by Su Jing in 659 CE, *Albizzia julibrissin* Dura treats five kinds of piles, harmonizes the five viscera, stops vomiting and neutralizes alcoholic poisoning and a poison of an iron nail.

The *Albizzia julibrissin* extract can be obtained from the bark, leaf, flower, root and seed of *Albizzia julibrissin*.

The *Albizzia julibrissin* extract is obtained by washing *Albizzia julibrissin*, completely drying the washed plant, physically crushing the dried plant, and extracting the crushed material with an extraction solvent. As the extraction solvent, any conventional extraction solvent can be used, and it is preferable to use a mixed solvent of 50% alcohol and water. The extract can be obtained by performing extraction at 80-100° C. for 1-8 hours and then evaporating ethanol. The solvent for the extraction of *Albizzia julibrissin* is used in a weight ratio of 1:2-6 with the respect to the crushed *Albizzia julibrissin*.

The *Cassia tora* extract is obtained in the same manner as the *Albizzia julibrissin* extract; however, a solvent for the extraction of *Cassia tora* is preferably used in a weight ratio of 1:1-4 with respect to the crushed *Cassia tora*. The *Cassia tora* extract can be obtained from the leaf, root, stem and flower of *Cassia tora*.

*Cassia* semen is the seed of *Cassia obtusifolia* L. or *Cassie tora* L., and in Chinese medicine, it is used as a peptic, intestinal antiseptic, diuretic or laxative agent. As recorded in Donguibogam (The Precious Mirror of Oriental Medicine, a comprehensive medical work written by Heo Jun in the Joseon Dynasty in 1610), drinking boiled *Cassie tora* is beneficial to the liver and improves eyesight. From *Cassie tora*, anthraquinones such as chrysophanol, emodin and physcion, anthraquinone glycosides such as obtusifolin, obtusin, chryso-obtusin, nor-rubrofusarin and rubrofusarin, were isolated and identified. From the seed thereof, emodin, obtusifolin and auran-thioobtusin ($C_{17}H_{14}O_7$) and glycosides thereof were isolated, and chrysophanol, chrysophanol anthrone, aloeemodin and rhein were confirmed by chromatography. Also, naphtopyron and glycosides thereof, such as rubrofusarin, nor-rubrofusarin, rubrofusarin gentiobiocide, isocoumarin toralactone, yellow pigment torachryson were isolated. Also, the leaf thereof contains kaempfefol-3-diglucoside ($C_{27}H_{30}O_{16}0.2H_2O$).

*Cassie tora* has the following effects: i) It has the effects of cleaning the liver and improving eyesight, ii) It has a blood pressure-lowering effect. In other words, when blood pressure is increased and not constant and the effect of an antihypertensive agent is not long-lasting, lesions can sometimes occur in the cardiovascular or cerebral vascular system, and in this case, the blood pressure-lowering effect can be obtained by enlarging coronary arteries. Also, when the long-term dosage of an antihypertensive drug is not effective due to essential hypertension, paralysis of one side can occur due to palsy caused by cerebral hemorrhage so that increased blood pressure can be continued and constipation can occur. In this case, drinking of boiled *Cassia tora* together with the administration of a suitable formulated drug can lower blood pressure and prevent constipation, iii) It has cholesterol-lowering effects, i.e., effects of preventing hypercholesterolemia caused by coronary arteriosclerosis.

The natural plant extract composition effective for the recovery and prevention of hyperlipidemia and stroke may further comprise other natural extracts, such as a *Schizandra chinensis* extract, a *Morus alba* extract or a licorice extract.

The *Schizandra chinensis* baillon, the fruit of *Schizandra chinensis*, is known to improve eyesight and is expected to be effective for fatigue recovery, because it contains organic acids, saponin, etc.

*Morus alba* L. is the young branch of *Morus alba* Linne or other closely related plants (*Moraceae*). It is long and cylindrical in shape, not constant in length, sometimes has side branches attached thereto and is 5-15 mm in diameter. Its outer surface is gray to gray-yellow in color and it has a yellow-brown viscous lenticel, and traces to which a petiole has been attached. Also, it has fine longitudinal wrinkles. It is hard and tough so as not to be easily broken, and the skin of broken parts is very thin and consists mostly of xylem. Its xylem is yellowish white in color and has radial patterns and its pith is white to yellowish white in color. The root bark thereof contains 0.15% mulberrin ($C_{25}H_{26}O_6$), 0.2% mulberrochromene ($C_{25}H_{24}O_6$), 0.2% cyclo-mulberrin ($C_{25}H_{24}O_6$), 0.016% cyclomulberrochromene ($C_{25}H_{22}O_6$), scopoletin, umbelliferon, trigonelline, tannin, flavonoid morucin, triterpenoid [alpha]-amirin, sitosterol-d-glucoside, betulic acid), adenine, betaine, palmitic acid, and stearic acid.

The fruit thereof mainly contains vitamins $B_1$, $B_2$ and C, oil (25% in seeds; mainly linolenic acid), anthocyanidin glycoside, non-saccharide cyanidin, chrysanthemin, 100% saccharides (glucose, maltose, sugar, and fructose), organic acids (malic acid, and citric acid), essential oil and isoquereitrin.

The xylem thereof contains 0.03% flavonoid morin ($C_{15}H_{10}O_7$), dihydromorin ($C_{15}H_{12}O_5$), maclurin (pentahydroxy benzoquinone; $C_{13}H_{10}O_6$) and the like. The root bark thereof acts to increase blood isoniazid concentrations and to maintain the increased concentrations, and thus has a good effect on the treatment of tuberculosis. A root bark extract and leaf extract thereof has a blood glucose lowering effect.

Licorice contains mild components, is sweet in taste, contains sweetening component glycyrrhizin, has antiallergic activity and NK cell-activating activity, and performs anti-inflammatory action by promoting the release of interferon. Also, it acts to inhibit the secretion of gastric acid and performs antiulcer action to protect the gastric mucous membrane. Also, it removes the toxicity of all drugs, suppresses a cough, digests phlegm, and neutralizes all drugs. In addition, it antagonizes various polar drugs or toxic drugs to treat drug poisoning caused by a powerful drug or a poison, and acts to neutralize a bacterial poison.

The natural plant extract composition may further comprise at least one selected from the group consisting of *Schizandra chinensis* extract, *Morus alba* extract or licorice extract. Said at least one plant extracted from the group consisting of *Schizandra chinensis* extract, *Morus alba* extract or licorice extract can be contained in a weight ratio of 1:0.1-2 with respect to the *Albizzia julibrissin* extract.

In addition, the natural plant extract composition may further comprise other natural plant extracts.

The natural plant extract composition may comprise 20-50 wt % of the *Cassia tora* extract, 10-70 wt % of the *Albizzia julibrissin* extract, and 10-20 wt % of at least one natural plant extract selected from the group consisting of *Schizandra chinensis* extract, *Morus alba* extract and licorice extract.

When the natural plant extract composition is added to functional food, it will preferably be used in an amount of 14-40 wt % based on the total weight of the food.

In another aspect, the present invention provides a method for preparing a natural plant extract composition for the treatment and prevention of hyperlipidemia and stroke, the method comprising the steps of: preparing a *Cassia tora* extract; preparing *Albizzia julibrissin* extract; and concentrating and mixing said extracts, in which said extracts are obtained by extraction in a mixed solvent of 50% alcohol and water at 80-100° C. for 1-8 hours.

Said method for preparing the natural plant extract composition may further comprise a step of preparing a *Schizandra chinensis* extract, preparing *Morus alba* extract or preparing licorice extract. The *Albizzia julibrissin* extract and the *Cassia tora* extract are preferably used after concentration.

As described above, in diseases of the circulatory system, hypercholesterolemia and an increase in blood low-density lipoprotein concentration are important factors of causing arteriosclerosis, and thus cause stroke. Also, the prevention of hyperlipidemia and stroke is more important than treatment after the onset thereof, and thus if cholesterol levels can be lowered by ingesting conventional food, hyperlipidemia and stroke can be prevented, and also can be treated as a result of the continued drinking of the food even after the onset thereof.

A general method to examine the reduction in cholesterol contents comprises analyzing the reduction in the contents of serum total cholesterol, LDL-cholesterol and triglyceride, which are associated with the induction of hyperlipidemia, as well as the increase in HDL-cholesterol, a factor of suppressing high cholesterol levels.

Hereinafter, the present invention will be described in further detail with reference to examples. It is to be understood, however, that these examples are not to be construed to limit the scope of the present invention.

Example 1

Preparation of *Albizzia julibrissin* Extract

The bark of *Albizzia julibrissin* was washed, completely dried and crushed. 5 g of the crushed *Albizzia julibrissin* was extracted in a mixture of 130 cc of 50% ethanol and 330 cc of water in an extractor at 95° C. for 6 hours, and the ethanol was then evaporated to obtain 300 cc of an *Albizzia julibrissin* extract. The plant was further extracted two times in the same manner as described above, thus obtaining *Albizzia julibrissin* extracts. The three *Albizzia julibrissin* extracts thus obtained were collected together and concentrated to a volume of ⅓ in a concentrator, thus obtaining 300 cc of a concentrated *Albizzia julibrissin* extract.

Example 2

Preparation of *Cassia tora* Extract

The seeds of *Cassia tora* were washed, completely dried and then crushed. 5 g of the crushed *Cassia tora* was extracted in the same manner as in Example 1, thus obtaining 300 cc of a concentrated extract.

Example 3

Preparation of *Schizandra chinensis* Extract

The leaf of *Schizandra chinensis* was washed, completely dried and then crushed. 5 g of the crushed plant was extracted in the same manner as in Example 1, thus obtaining 300 cc of a concentrated extract.

Example 4

Preparation of *Morus alba* Extract

*Morus alba* was washed, completely dried and then crushed. 5 g of the crushed plant was extracted in the same manner as in Example 1, thus obtaining 300 cc of a concentrated extract.

Example 5

Preparation of Licorice Extract

Licorice was washed, completely dried and then crushed. 5 g of the crushed plant was extracted in the same manner as in Example 1, thus obtaining 300 cc of a concentrated extract.

Examples 6-10

The extracts prepared in Examples 1 to 5 were mixed with each other to have components and contents shown in Table 1 below, thus preparing natural plant extract compositions.

TABLE 1

Preparation of natural plant extract compositions (unit: wt %)

|  | Albizzia julibrissin extract | Cassia tora extract | Schizandra chinensis extract | Morus alba extract | licorice extract |
|---|---|---|---|---|---|
| Example 6 | 50 | 50 |  |  |  |
| Example 7 | 30 | 40 | 10 | 10 | 10 |
| Example 8 | 30 | 30 | 20 | 10 | 10 |
| Example 9 | 20 | 50 | 10 | 10 | 10 |
| Example 10 | 40 | 20 | 20 | 10 | 10 |

Examples 11-15

Preparation of Natural Teas (Unit: wt %)

TABLE 2

|  | Composition of Example 6 | Composition of Example 7 | Water | Antioxidant vitamin E | Other food additives |
|---|---|---|---|---|---|
| Example 11 | 2 |  | Balance | 4 | Small amount |
| Example 12 |  | 1.5 | Balance | 6 | Small amount |
| Example 13 | 3 |  | Balance | 3 | Small amount |
| Example 14 | 1.5 |  | Balance | 6 | Small amount |
| Example 15 | 4 |  | Balance | 4 | Small amount |

Test Example 1

Test Subjects

Fifty hyperlipidemia patients (20 men and 30 women) who have agreed to participate in the study were randomly grouped into two groups each consisting of 25 persons: a group administered with the inventive composition; and a group administered with a placebo.

1) The average ages of the two groups were 56.1+−2.8 years old for the group administered with the inventive composition, and 57.1+2.3 years old for the group administered with the placebo, and the ratios of men in the two groups were 40.9% (n=9) for the group administered with the inventive composition, and 42.1% (n=8) for the group administered with the placebo.

2) Height, body weight, BNI and WHR were all similar between the two groups, and there was no significant difference in blood pressure between the two groups.

3) There was no significant difference in the ratio of current drinkers, the ratio of current smokers, nutrient intake, and stress, between the two groups, but the ratio of persons who take health food was significantly higher in the group administered with the placebo (p<0.05). Regardless of the time point before or after the administration of the inventive composition and the placebo, there was a difference in the ratio of drinkers, the ratio of current smokers, the ratio of persons who take nutrients, and stress, between the two groups, and there was no significant difference in details other than the intake of health food between the two groups.

4) At the start of examination, the score of eating habits and the score of food intake frequency had no difference between the two groups. Also, the score of eating habits after the administration of the inventive composition and the placebo was similar to that before the administration, but the score of food intake frequency was slightly increased in the case of the group administered with the placebo. However, there was no significant difference between the two groups.

Placebo

To 200 ml of water, 2.5 g of maltodextrin and 0.5 g of an excipient were added and an edible pigment was added thereto to show a color similar to that of the inventive natural tea.

Test Method

The natural tea of Example 13 of the present invention and the placebo were administered for 2 months, and a blood test and a biochemical test were repeatedly performed at one month and two months after the experiment. In the experiment, the test subjects were permitted to drink 140 cc of each of the inventive composition and the placebo daily.

Before and after the administration of the extract composition of Example 13 and the placebo, blood was collected with a syringe and coagulated. The coagulated blood was centrifuged at 1000 rpm, and then serum was collected from the blood and measured for cholesterol levels. The measurement of cholesterol levels was performed by the enzymatic reaction of cholesterol oxidase (CO), cholesterol esterase (CE) and peroxidase (POD) using a total cholesterol measurement kit (Boehringer mannhein Germany), an HDL-cholesterol measurement kit (Boehringer mannhein, Germany) and a biochemical autoanalyzer (Hitachi 747, Japan).

The measurement results are shown in Table 3 below.

TABLE 3

|  |  | Before administration Mean ± SE | 2 months after administration Mean ± SE | Difference Mean ± SE |
|---|---|---|---|---|
| Triglyceride | Placebo | 178.3 ± 9.5 | 157.5 ± 8.8 | −17.2 ± 19.6 |
|  | Example 11 | 248.4 ± 35.4 | 197.6 ± 29.3 | −50.5 ± 28.8 |
| Total cholesterol | Placebo | 225.4 ± 10.2 | 216.5 ± 7.4 | −8.5 ± 5.6 |
|  | Example 11 | 222.6 ± 12.1 | 204.4 ± 7.3 | −18.2 ± 9.4 |
| HDL-C[1] | Placebo | 46.3 ± 2.3 | 45.3 ± 2.5 | −1.0 ± 1.4 |
|  | Example 11 | 42.1 ± 1.6 | 43.4 ± 2.2 | 1.3 ± 1.2 |
| LDL-C[2] | Placebo | 146.0 ± 5.5 | 138.2 ± 6.0 | −7.8 ± 5.0 |
|  | Example 11 | 142.1 ± 10.1 | 133.0 ± 7.1 | −9.1 ± 6.5 |
| Apo A1 | Placebo | 137.0 ± 5.6 | 127.7 ± 4.5 | −9.3 ± 2.7 |
|  | Example 11 | 121.5 ± 7.5 | 128.0 ± 5.8 | 6.5 ± 5.2 |
| Apo B | Placebo | 120.2 ± 3.7 | 109.5 ± 4.1 | −10.7 ± 4.7 |
|  | Example 11 | 121.2 ± 6.8 | 103.5 ± 4.6 | −17.7 ± 5.8 |

(mg/dl)

As can be seen in Table 3, the group administered with the natural tea of Example 11 according to the present invention showed a reduction of 50 mg in serum triglyceride, and the group administered with the placebo also a reduction in serum triglyceride, but the degree of the reduction was 17 mg which was very low compared to that of the group administered with the inventive tea.

As shown in Table 3, the serum cholesterol level was continuously decreased in the group administered with the inventive natural tea and the group administered with the placebo, at 1 month and 2 months after the administration. However, the group administered with the inventive natural tea showed a 18-fold larger decrease in the serum cholesterol level than that of the group administered with the placebo.

As shown in Table 3, the level of HDL-cholesterol, a factor of suppressing high cholesterol levels, showed a tendency to slightly decrease at 2 months after the administration in the case of the group administered with the placebo, whereas the group administered with the natural tea of Example 11 of the present invention showed an increase of 5.1 mg in Apo Al, a typical apolipoprotein contained in HDL. Based on a high relationship (relationship coefficient r=0.90146) between HDL-cholesterol and Apo Al levels, this increase in Apo Al can be considered as the increase in the HDL-cholesterol level.

The LDL-cholesterol level was decreased in the two groups, but was decreased for the first one month of the experiment and then increased, whereas it was continuously decreased in the group administered with the inventive natural tea. The level of Apo B, the apolipoprotein of LDL-cholesterol, was also significantly decreased in the both two groups, but was more decreased in the group administered with the inventive natural tea. This suggests that the administration of the inventive natural tea resulted in the decrease in the LDL level.

Test Example 2

Changes in Blood Glucose and Other Serum Indices

According to the same method as in Test Example 1, the test subjects were divided into group C administered with the inventive natural tea and group D administered with Comparative Example 1. The groups C and D were administered with the inventive natural tea and the placebo, respectively, according to the same method as in Test Example 1.

Before and after the administration of the natural tea of Example 11 according to the present invention and the placebo, the changes in fasting blood sugar (FBS), HbAlc, BUN, creatinine, AST and ALT levels were measured according to a conventional method. The measurement results are shown in Table 4 below.

TABLE 4

|  |  | Before administration Mean ± SE | After administration (after 2 months) Mean ± SE | Difference Mean ± SE |
|---|---|---|---|---|
| FBS (mg/dl) | Placebo | 225.3 ± 10.2 | 223.9 ± 7.5 | −1.4 ± 5.6 |
|  | Example 11 | 218.9 ± 11.1 | 203.9 ± 6.6 | −15.0 ± 9.5 |
| HbAlc (%) | Placebo | 7.7 ± 0.4 | 7.5 ± 0.3 | −0.2 ± 0.2 |
|  | Example 11 | 7.8 ± 0.4 | 7.7 ± 0.4 | −0.1 ± 0.2 |
| BUN (mg/dl) | Placebo | 16.0 ± 0.7 | 15.1 ± 0.9 | −1.1 ± 0.9 |
|  | Example 11 | 13.0 ± 1.5 | 12.3 ± 1.3 | −0.7 ± 1.0 |
| Creatinine | Placebo | 0.88 ± 0.04 | 0.93 ± 0.03 | 0.05 ± 0.03 |
|  | Example 11 | 0.95 ± 0.06 | 1.00 ± 0.07 | 0.05 ± 0.04 |
| AST (IU/L) | Placebo | 21.0 ± 1.5 | 20.0 ± 0.9 | −1.0 ± 1.3 |
|  | Example 11 | 25.6 ± 1.8 | 27.0 ± 3.7 | 1.4 ± 4.0 |
| ALT (IU/L) | Placebo | 32.0 ± 4.8 | 26.9 ± 2.4 | −5.1 ± 4.0 |
|  | Example 11 | 31.6 ± 3.5 | 33.0 ± 4.7 | −1.4 ± 3.4 |

As can be seen in Table 4 above, the fasting blood level was decreased in both the two groups compared to before the administration, but it was more greatly decreased in the group administered with the inventive natural tea.

The HbAlc level was also decreased in both the two groups, but had no significant difference between the two groups.

Also, it can be seen that the blood urea nitrogen (BUN) level was decreased in both the two groups, and the creatinine level was slightly decreased in both the two groups, but had no significant difference between the two groups. Also, there was no significant change in the AST and ALT levels.

As can be seen from the above-described test results, the natural tea composition according to the present invention can lower the blood cholesterol level to prevent arteriosclerosis and also can prevent stroke, which is caused by the increase in the blood cholesterol content. Also, it allows recovery from the disease through the continued drinking thereof even after the onset of the disease, and when prepared into a drink, it is easy to drink so that it can be taken at ordinary times, and thus is effective for the prevention and treatment of hyperlipidemia and stroke.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A plant 50% ethanolic extract composition for the recovery and prevention of hyperlipidemia and stroke comprising 20-50 wt % of a *Cassia tora* 50% ethanolic extract, 10-65 wt % of an *Albizzia julibrissin* extract, 5-20 wt % of a *Schizandra chinensis* 50% ethanolic extract, 5-20 wt % of a *Morus alba* 50% ethanolic extract and 5-20 wt % of a licorice extract.

2. The composition of claim 1, wherein the *Albizzia julibrissin* 50% ethanolic extract contains quercitrin.

3. The composition of claim 1, wherein the *Cassia tora* 50% ethanolic extract contains obtusin ($C_{18}H_{16}O_7$).

4. The composition of claim 1, wherein the plant 50% ethanolic extract composition additionally comprises at least one selected from the group consisting of *Schizandra chinensis* 50% ethanolic extract and licorice extract.

5. The composition of claim 1, wherein the *Albizzia julibrissin* 50% ethanolic extract and *Morus alba* 50% ethanolic extract can be contained in a weight ratio of 1:0.1-1:2.

6. The composition of claim 1, wherein the plant 50% ethanolic extract composition comprises 20-50 wt % of the *Cassia tora* extract, 10-70 wt % of the *Albizzia julibrissin* 50% ethanolic extract, and 10-20 wt % of *Morus alba* extract.

7. The composition of claim 1, wherein the *Cassia tora* 50% ethanolic extract and the *Albizzia julibrissin* extract are contained in a weight ratio of 1:0.3-5.

8. The composition of claim 7, wherein the plant extract composition is prepared using a mixed solvent of 50% ethanol and water in a weight ratio of 1:1-3.

9. The composition of claim 8, wherein plant extracts are prepared by extraction at 80-100° C. for about 1-8 hours.

10. The composition of claim 1, wherein the plant extract composition is prepared by extracting each of the plants 1-3 times, mixing the extract fractions with each other and concentrating the mixture before use.

11. The composition of claim 1, wherein the *Albizzia julibrissin* 50% ethanolic extract is prepared using the bark, leaf, flower, root and seed of *Albizzia julibrissin*.

12. The composition of claim 1, wherein the *Albizzia julibrissin* 50% ethanolic extract is prepared using a mixed solvent of 50% ethanol and water in a weight ratio of 1:1.5 in 2-6 times by weight to crushed *Albizzia julibrissin*.

* * * * *